United States Patent [19]

Raftopoulos

[11] 4,436,099

[45] Mar. 13, 1984

[54] INSTRUMENT FOR MEASURING THE RANGE OF MOTION ASSOCIATED WITH A HUMAN BODY JOINT

[75] Inventor: Demetrios D. Raftopoulos, Toledo, Ohio

[73] Assignee: The University of Toledo, Toledo, Ohio

[21] Appl. No.: 292,899

[22] Filed: Aug. 14, 1981

[51] Int. Cl.$^3$ .............................................. A61B 5/10
[52] U.S. Cl. ..................................... 128/782; 128/774
[58] Field of Search ................. 128/774, 782; 33/1 N, 33/1 CC, 1 PT, 174 D, 174 N, 180 R

[56] References Cited

U.S. PATENT DOCUMENTS

| | | | |
|---|---|---|---|
| 1,590,499 | 6/1926 | Cozad | 33/174 D |
| 3,020,639 | 2/1962 | Karpovich et al. | 33/1 N |
| 4,034,745 | 7/1977 | Bloom | 128/706 |
| 4,306,571 | 12/1981 | McLeod, Jr. | 128/782 |
| 4,318,225 | 3/1982 | Jenkinson | 33/1 PT |

OTHER PUBLICATIONS

Townsend, M. A. et al., "Total Motion Knee Goniometry", *J. Biomechanics*, vol. 10, No. 3, (1977), pp. 183-193.
Chao, E. Y. S., et al., "Instrumented Measurement of Human Joint Motion", *ISA Transactions*, vol. 17, No. 1, (1978), pp. 13-19.
Kettlekamp, D. B. et al., "An Electrogoniometric Study of Knee Motion in Normal Gait, " *Journ. of Bone & Joint Surg.*, vol. 52-A, No. 4, Jun. 1970, pp. 775-790.
Chao, E. Y., An, K. N., Askew, L. J., Morrey, B. F., "Electrogoniometer for the Measurement of Human Elbow Joint Rotation," *Journal of Biomechanical Engineering*, vol. 102, No. 4, (Nov. 1980), pp. 301-310.

*Primary Examiner*—Kyle L. Howell
*Assistant Examiner*—Christine A. Fukushima
*Attorney, Agent, or Firm*—Wilson, Fraser, Barker & Clemens

[57] ABSTRACT

The present invention relates to an instrument for measuring the range of angular displacement associated with two human body portions connected to a common joint. The instrument includes two pivotally connected, elongate rods, and separate supports for supporting each of the rods on a respective one of the body portions in spaced relationship with the body portion. Each of the supports includes a pair of ball and socket assemblies which are mounted on the respective body portions in spaced relation to one another. The ball of each ball and socket assembly has an aperture formed therethrough for receiving the associated elongate rod. Such a support arrangement enables the body portions to be rotated about the common joint without affecting the natural movements of the body portions. An encoder is utilized to pivotally connect the two elongate rods and to generate an electrical output signal representing the relative angular position between the two rods. A counter and display circuit is responsive to the encoder output signal for determining the change in angular position between the two rods and displaying this value in terms of angular degrees.

11 Claims, 11 Drawing Figures

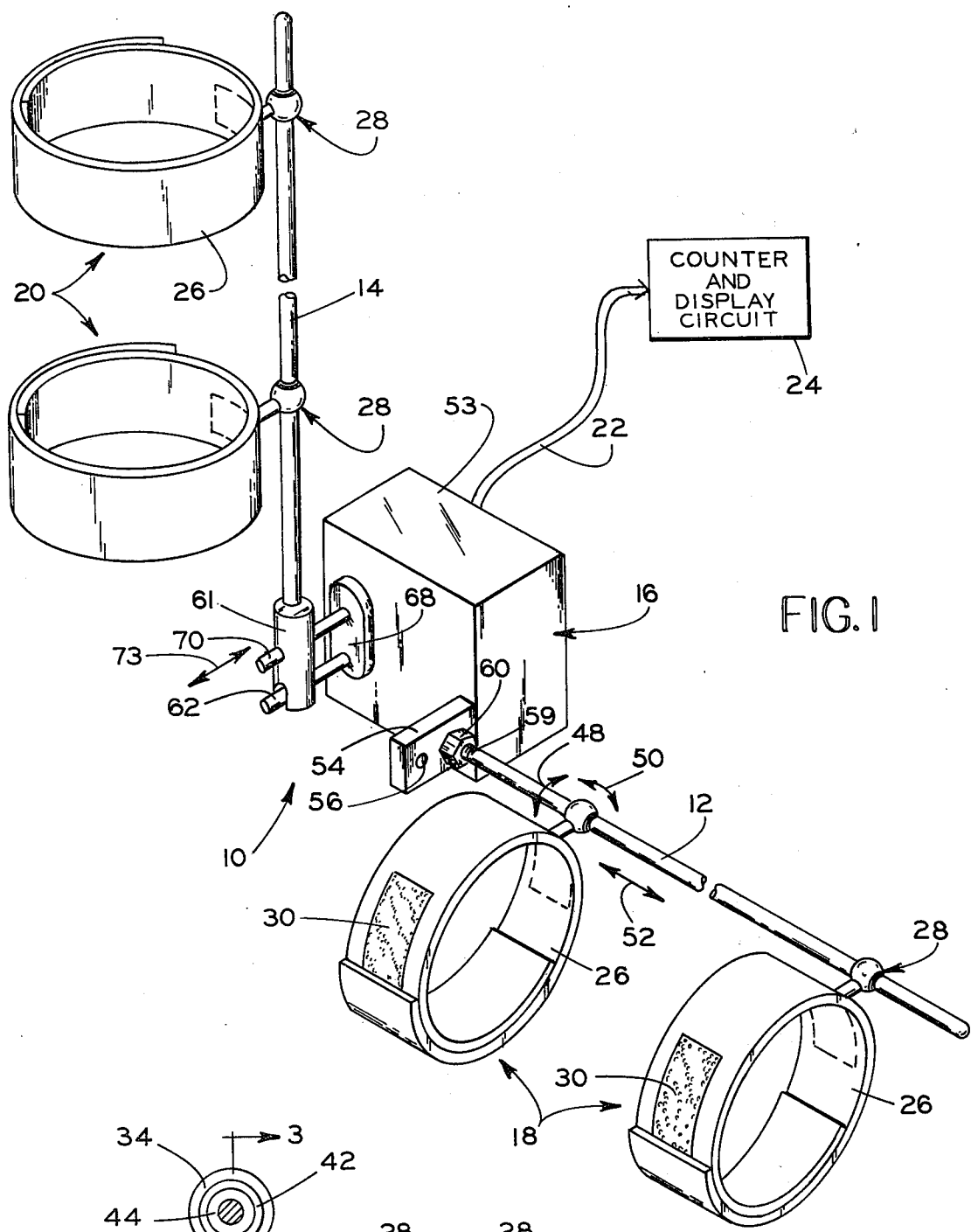

INSTRUMENT FOR MEASURING THE RANGE OF MOTION ASSOCIATED WITH A HUMAN BODY JOINT

BACKGROUND OF THE INVENTION

During the last forty years, researchers and therapists have been actively involved in designing improved methods for measuring the amount of angular rotation between two human body portions connected to a common joint. In an article entitled "Measurement Of Joint Motion," found in *Archives of Physical Medicine*, pages 416–423, July, 1945, Catherine West discusses an instrument consisting of a large protractor which can be used to measure the range of motion associated with a body joint. In using the protractor, one would align the axis of a joint with the center of the protractor. By noting the initial and final protractor readings, one could subjectively determine the angular displacement between the two body portions.

An improvement on this instrument is disclosed in an article written by M. D. Moore entitled "The Measurement Of Joint Motion, Part III: Technique of Goniometry," found in *Physical Therapy Review*, Volume 29, pages 256–264, June, 1949. Moore discloses a goniometer which is designed to utilize the anatomical zero point as a starting position for all measurements. In this device, the stationary arm of the instrument is aligned with the proximal portion of a limb, while the moving arm of the instrument is aligned with the distal portion. While the Moore instrument is an improvement over the West protractor, both of the devices suffer from the difficulty in subjectively aligning the instrument with the body portions.

An article entitled "A Simple Objective And Reliable Measure of Flexibility," by Jack Leighton and published in *Research Quarterly*, Volume 13, pages 205–216, May, 1942, discloses a measuring instrument which can be strapped directly to the body portions, thereby avoiding the need to subjectively align the instrument. The instrument consisted of a 360° dial and an associated weighted pointer connected to one body portion. The total range of motion of the one body portion moving against gravity was recorded on the dial. Although this instrument was capable of measuring the range of motion associated with a joint by starting from the extreme position in one direction and ending at the terminal point of movement in the other direction, it was not capable of measuring single joint flexion or extension from the anatomical zero point.

Peter V. Karpovich, in *Physiology Of Muscular Activity*, Philadelphia: W. B. Saunders Company, 1965, on page 38 discusses an electro-goniometer which provides a continual recording to the angular displacement between two body portions connected to a common joint. The electrogoniometer utilizes a potentiometer for measuring the angular position between the two body portions. One of the problems associated with this instrument is the fact that the instrument is supported on the body portions in such a manner which may alter normal movement of the body portions which typically requires torsion and cross plane motion.

SUMMARY OF THE INVENTION

The present invention relates to an instrument for measuring the amount of angular displacement between two human body portions connected to a common joint. The instrument includes two pivotally connected, elongate rods, and a separate support means for supporting each of the rods on a respective one of the body portions in generally spaced relationship with the body portion.

Each of the support means comprises a pair of ball ans socket assemblies for supporting the respective elongate rod at two predetermined points along the respective body portion. Each assembly has an aperture formed through the ball to receive the associated rod. The ball and socket assemblies permit the elongate rod to rotate about its longitudinal axis, to pivot in any direction relative to the assembly, and also to move longitudinally with respect to the body portion. The two predetermined points along the body portion at which the ball and socket assemblies are to be positioned are selected in order to establish the desired spaced relationship between the body portion and the associated elongate rod. Such a support arrangement enables the body portions to be rotated about the common joint without affecting the natural movements of body portions.

The present invention utilizes an encoder as a means for pivotally interconnecting the two elongate rods. As the rods are pivoted relative to one another, the encoder generates an electrical output signal representing the relative angular position between the two rods. A counter and display circuit is responsive to the encoder output signal for determining the change in angular position between the two rods and displaying this value in terms of angular degrees.

BRIEF DESCRIPTION OF THE DRAWINGS

FIG. 1 is a perspective view of the measuring instrument according to the present invention;

FIG. 2 is an elevational view, partly in section, illustrating one of the ball and socket assemblies utilized to support the elongate rods of FIG. 1;

FIG. 3 is a sectional view taken along line 3—3 of FIG. 2;

DESCRIPTION OF THE PREFERRED EMBODIMENT

Figure 4:
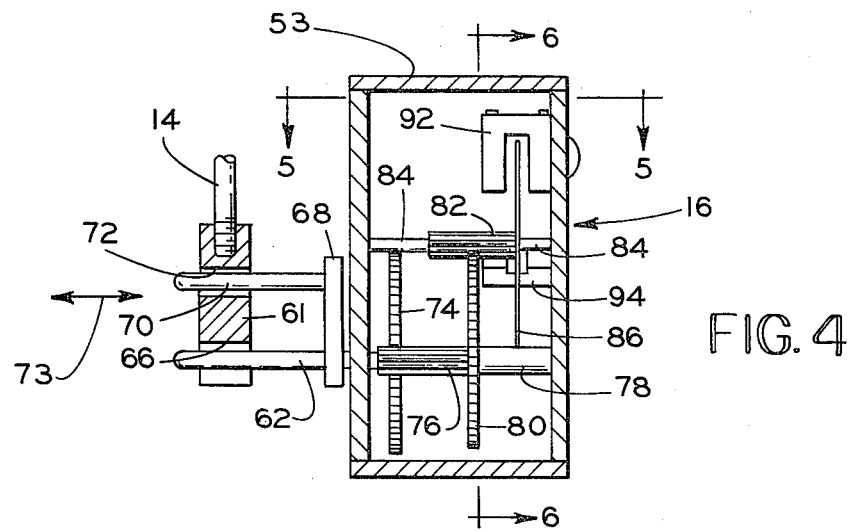
FIG. 4 is a sectional view of the encoder of FIG. 1, taken along the line 4—4 of FIG. 5.

Referring to FIG. 1, there is shown a perspective view of a measuring instrument, generally indicated by numeral 10, embodying the features of the present invention. It should be noted at the outset of this description that the measuring device shown in FIG. 1 is designed specifically for measuring the range of motion associated with either an elbow joint or a knee joint. It will become readily apparent to one skilled in the art on how the instrument shown in FIG. 1 can be adapted for use to measure the range of motion of other body joints, for example, shoulder joints, hip joints, wrist joints, finger joints, and ankle joints.

The measuring instrument 10 includes two elongate rods 12 and 14 which are pivotally interconnected by means of an encoder 16. The elongate rods 12 and 14 have support means 18 and 20, respectively, mounted thereon for supporting the two elongate rods on two body portions (not shown in FIG. 1) connected to a common joint. As the rods 12 and 14 are pivoted relative to one another, the encoder 16 generates an electrical signal on lines 22 representing the relative angular position between the two rods. This signal is supplied to a counter and display circuit 24. The circuit 24 is responsive to the signal on the lines 22 for determining the change in angular position between the two rods and displaying this value in terms of angular degrees.

In FIG. 1, the support means 18 and 20 are basically identical. Each of the support means 18 and 20 includes a pair of flexible straps 26 each of which is fastened to the associated elongate rod by means of a ball and socket assembly 28. The flexible strap 26 can be constructed of a cloth material and can include a Velcro-type fastening portion 30 to provide a means for securely positioning the ball and socket assembly 28 relative to an associated body portion.

The ball and socket assembly 28 is shown in more detail in FIGS. 2 and 3. The assembly 28 includes a main body extension 32 having an enlarged portion 34 on one end and a plate portion 36 secured to the opposite end to provide a means for fastening the assembly 28 to the flexible strap 26. As shown in FIG. 3, the plate portion 36 can be positioned between two cloth ribbons 38 and 40 which can be stitched along their marginal edges to form the flexible strap 26.

The enlarged end portion 34 of the main body extension 32 has a cylindrical aperture formed therethrough for receiving a socket 42 having a rotatable ball 44 mounted therein. Typically, the socket 42 is press-fit into the enlarged end portion 34. The ball 44 has a centrally disposed, cylindrical aperture 46 with an inner diameter slightly larger than the outer diameter of the elongate rod 12. The ball and socket assembly 28 permits the elongate rod 12 to rotate about its longitudinal axis within the cylindrical aperture 46 as represented by direction arrows 48 in FIG. 1, and also permits the rod 12 and the ball 44 to pivot within the socket 42 as represented by direction arrows 48 and 50. The elongate rod 12 can also slide longitudinally relative to the assembly 28 along the axis of the rod as shown by the direction arrows 52.

As previously mentioned, each of the support means 18 and 20 include a pair of flexible straps 26 with associated ball and socket assemblies 28. This type of structure provides a two point support of the elongate rod relative to the body portion. As will be discussed, this two point support structure along with the wide variety of movements provided by the ball and socket assemblies 28 maintains the elongate rod in a predetermined spaced relation relative to the body portion without limiting the natural movements of the body portion.

Figure 5:
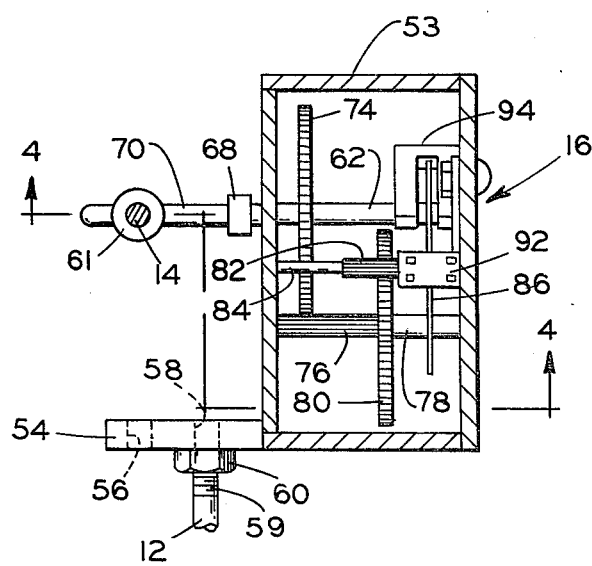
FIG. 5 is a sectional view of the encoder taken along line 5—5 of FIG. 4.
Figure 6:
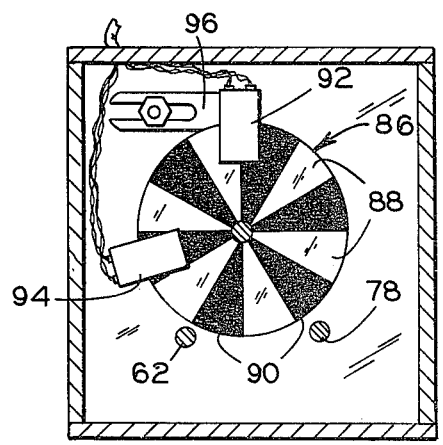
FIG. 6 is a sectional view of the encoder taken along the line 6—6 of FIG. 4.

The encoder 16 of FIG. 1 is shown in more detail in FIGS. 4, 5, and 6. FIG. 5 illustrates the manner in which the end portion of the elongate rod 12 is attached to the encoder 16. The encoder 16 includes a housing 53 which is provided with an extension portion 54 having a pair of internally threaded apertures 56 and 58 formed therein for receiving a threaded end 59 of the elongate rod 12. A lock nut 60 is utilized to securely mount the rod 12 to the extension portion 54. As will be discussed, threaded apertures 56 and 58 provide a means for adjusting the plane of rotation of the elongate rod 12.

FIG. 4 illustrates the manner in which the end portion of the elongate rod 14 is mounted to the encoder 16. The end of the elongated rod 14 is threadably secured to an enlarged cylindrical end portion 61. The encoder 16 includes a rotatable input shaft 62 which extends outwardly from the side wall of the housing 53 and is received within an inverted U-shaped cutout 66 formed in the lower end of the cylindrical end portion 61. A support member 68 extends radially from the input shaft 62 and is utilized to support a stabilizing pin 70 in generally parallel relationship with the input shaft 62. The stabilizing pin 70 extends outwardly from the support member 68 and into an aperture 72 formed through the end portion 61. Mounting the elongate rod 14 to the encoder 16 in this manner permits the plane of rotation of the rod 14 to vary as the rod is pivoted about the longitudinal axis of the input shaft 62. This movement is represented by direction arrows 73 shown in FIGS. 1 and 4.

The input shaft 62 extends through the interior of the housing 53 and is supported for rotational movement by the side walls of the housing 53. The input shaft 62 supports a first drive gear 74 which is coupled to a first pinion gear 76 mounted on a rotatable intermediate shaft 78. A second drive gear 80 is fixed to the shaft 78 and is coupled to a second pinion gear 82 mounted on a rotatable output shaft 84. The output shaft 84 has a partially transparent, partially opaque, segmented disc 86 mounted thereon for rotation therewith.

As shown in FIG. 6, the disc 86 includes six transparent segments 88 alternately spaced between six opaque segments 90. A pair of optical couplers 92 and 94 are mounted on a side wall of the housing 53 and are positioned to monitor the rotation of the segmented disc 86. The optical coupler 94 is securely fixed relative to the segmented disc 86, while the optical coupler 92 is provided with a mounting bracket 96 having an elongated slot formed therein to provide a means for fine positioning of the coupler 92 relative to the segment disc 86.

As previously mentioned, the encoder 16 generates an electrical signal represeting the relative angular position between the two elongate rods 12 and 14. Specifically, this electrical signal consists of a series of pulses, with each pulse representing a predetermined amount of rotation of the input shaft. In order to simplify the electronics associated with the instrument, the input to output ratio between the input shaft 62 and the output shaft 84 is selected with a ratio of 1:60. Thus, for each complete revolution of the input shaft 62, the segmented disc 86 will make sixty revolutions. Since the segmented disc 86 is provided with six opaque segments 90, an opaque segment will pass the optical couplers 92 and 94 three hundred and sixty times for each complete revolution of the input shaft 62. As will be discussed, each of the optical couplers 92 and 94 function to generate an electrical pulse each time an opaque segment of the disc 86 passes the coupler. Hence, each pulse generated by one of the couplers will represent one degree of rotation of the input shaft.

It should be noted that, in certain instances, it may be desirous to provide a measuring instrument having an accuracy greater than the one degree accuracy provided by the above described encoder. In these instances, the encoder 16 could be modified to generate a pulse train in which each pulse represents less than one degree of rotation. Also, in instances when less than one degree accuracy is suitable, a rotary potentiometer (not shown) may be utilized instead of the encoder 6.

Figure 7:
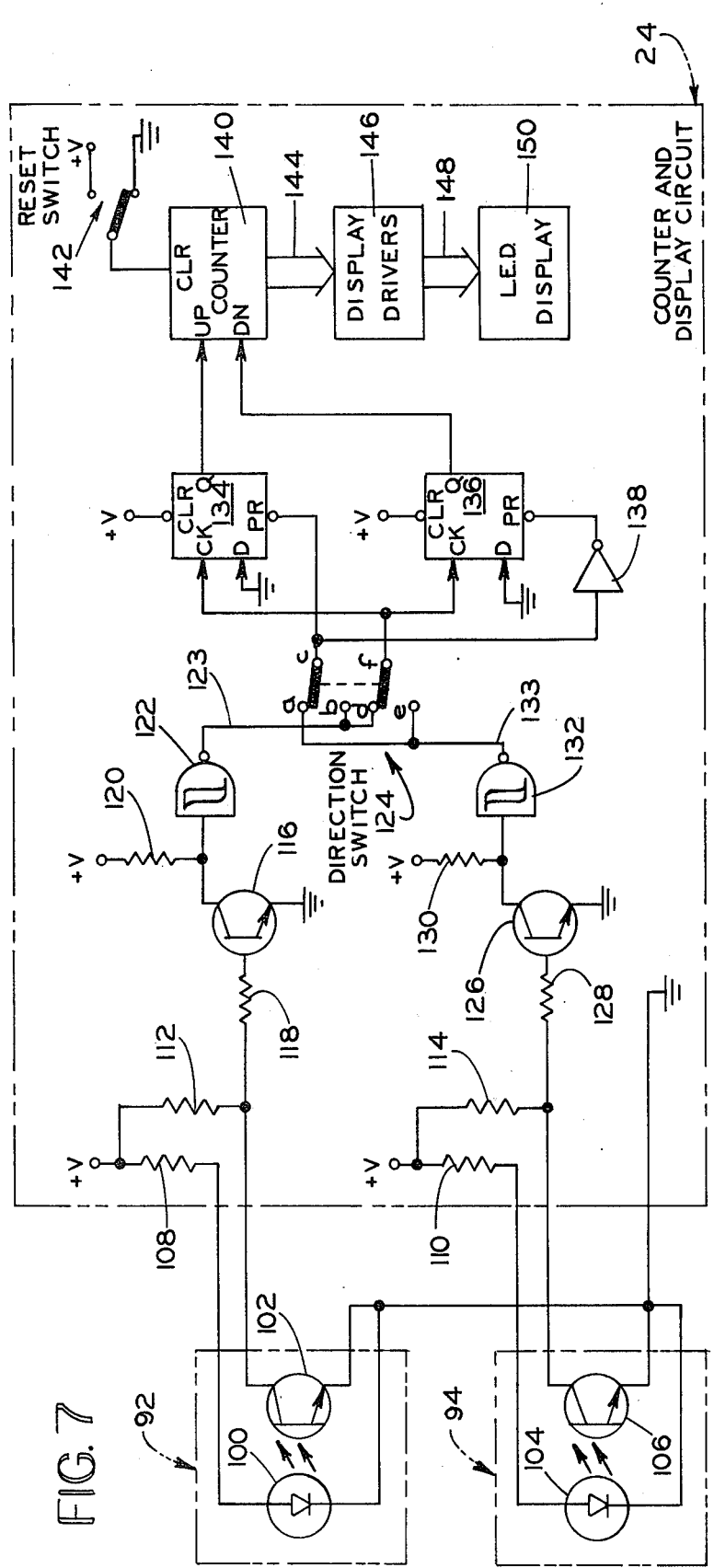
FIG. 7 is a schematic diagram illustrating the counter and display circuit of FIG. 1.

Referring to FIG. 7, there is shown an electrical schematic of the optical couplers 92 and 94 in the encoder 16, along with a block diagram of the counter and display circuit 24 of FIG. 1. The optical coupler 92 is represented as a light emitting diode (LED) 100 which is maintained in spaced relationship with an associated NPN phototransistor 102. The optical coupler 94 is similar to the coupler 92 and includes an LED 104 and an associated NPN phototransistor 106. The anodes of the LEDs 100 and 104 are connected to a +V power supply through resistors 108 and 110, respectively. The collectors of the phototransistors 102 and 106 are connected to the +V power supply through resistors 112 and 114, respectively. The cathodes of the LEDs 100 and 104 and the emitters of the phototransistors 102 and 106 are all connected to the circuit ground potential. The electrical connections between the optical couplers 92 and 94 and the circuit 24 represent the lines 22 of FIG. 1.

The collector of the phototransistor 102 is also connected to the base of an NPN transistor 116 through a resistor 118. The transistor 116 has a collector connected to the +V power supply through a resistor 120 and an emitter connected to the circuit ground potential. The collector of the transistor 116 is also connected as an input to a first Schmitt trigger 122 having an output connected to the b and d terminals of a double pole, double throw direction switch 124.

The collector of the phototransistor 106 is connected to the base of an NPN transistor 126 through a resistor 128. The transistor 126 a collector connected to the +V power supply through a resistor 130 and an emitter connected to the circuit ground potential. The collector of the transistor 126 is also connected as the input to a second Schmitt trigger 132 having an output connected to the a and e terminals of the direction switch 124.

As previously mentioned, the optical couplers 92 and 94 each function to generate an output pulse train with each pulse representing a predetermined amount of rotation of the input shaft 62. The segmented disc 86 shown in FIG. 6 rotates between the LED and the phototransistor of each optical coupler such that, when a transparent segment 88 is positioned between the LED and the associated phototransistor, the light generated by the LED will pass through the transparent segment and be applied to the base of the respective phototransistor. This causes the phototransistor to turn on such that a signal near ground potential is generated at the emitter of the phototransistor. In the case of the optical coupler 92, this near-ground potential is supplied to the base of the transistor 116 to turn off the transistor 116. When an opaque segment 90 is positioned between the LED 100 and the transistor 102, the tansistor 102 will be off such that a positive polarity signal is applied to the base of the transistor 116 to turn on the transistor 116 and apply a positive polarity signal to the input of the Schmitt trigger 122. The transistor 116 and the Schmitt trigger 122 function to condition the pulses generated by the optical coupler 92 to provide a clean, square waveform for the counting circuitry.

The input circuitry in the circuit 24 associated with the optical coupler 94 operates in a manner similar to the input circuitry associated with the optical coupler 92. However, the optical coupler 94 is positioned relative to the segmented disc 86 and the other optical coupler 92 such that the output pulse train of the coupler 94 will lag the output pulse train of the coupler 92 by a predetermined amount.

Figure 8:
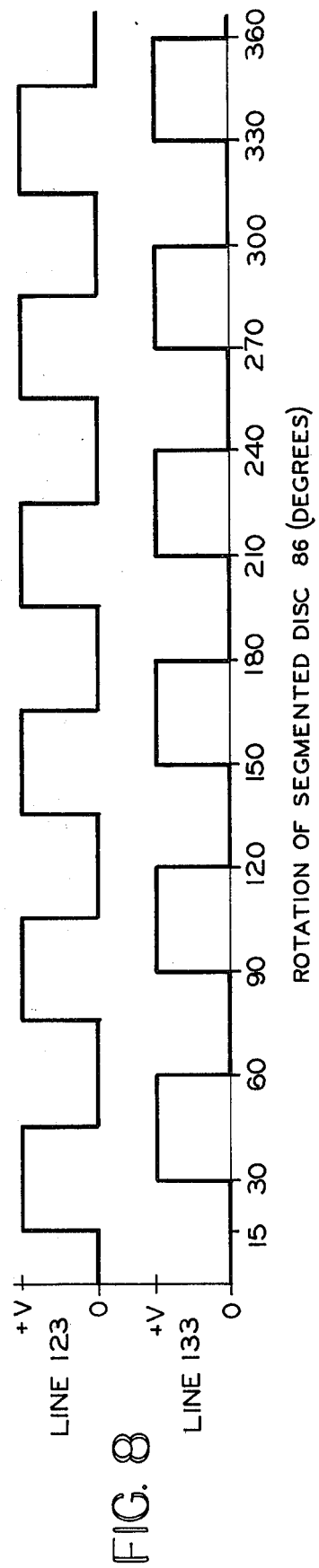
FIG. 8 is a waveform diagram representing two of the waveforms generated by the circuit of FIG. 7.

The waveform diagram of FIG. 8 illustrates the waveforms which appear on the output lines 123 and 133 of the Schmitt triggers 122 and 132, respectively, during one complete revolution of the segmented disc 86. The upper waveform in FIG. 8 represents the output of the first Schmitt trigger 122, while the lower waveform represents the ooutput of the second Schmitt trigger 132. As shown in FIG. 8, the waveform on the line 133 associated with the coupler 94 lags that of the waveform on the line 123 associated with the coupler 92 by approximately 15°. It should be noted that the amount of lag between the two waveforms is not critical. As will be discussed, the use of two optical couplers in the encoder 16 along with the lag between the two pulse trains enables the counter and display circuit to distinguish between clockwise and counterclockwise rotation of the input shaft 62.

If the input shaft 62 is to be rotated in one direction, the direction switch 124 is set in the upper position, and if the input shaft is to be rotated in an opposite direction, the switch is set in the lower position. The terminal c of the switch 124 is connected to a preset (PR) input of a first D-type flip-flop 134 and to a preset input of a second D-type flip-flop 136 through an inverter 138. The terminal F of the direction switch 124 is connected to the clock (CK) inputs of the flip-flops 134 and 136. Both the flip-flops 134 and 136 have D inputs connected to the circuit ground potential and clear (CLR) inputs connected to the +V power supply. The output terminal (Q) of the flip-flop 134 is connected to an UP input of a binary counter 140, while the output terminal (Q) of the flip-flop 136 is connected to a DOWN input of the counter 140.

The counter 140 has a clear (CLR) input which is connected to the circuit ground potential through a reset switch 142. When it is desired to clear the counter 140, the switch 142 is momentarily actuated to supply a +V potential to the counter clear input. The counter 140 monitors the output of the flip-flops 134 and 136 and generates an output count on lines 144 to a group of display drivers 146. The display drivers 146 are utilized to generate drive signals on lines 148 to enable the LED display 150. Typically, the display 150 will comprise a group of three, seven-segment LED indicators (not shown).

The D-type flip-flops 134 and 136 function to generate an output signal at terminal (Q) at logic "0" whenever the preset input is at logic "1" and a "0" to "1" transition occurs at the clock input. Whenever the preset output is at logic "0", the flip-flop is essentially disabled and the output of the flip-flop will be at logic "1", regardless of the signal present at the clock input. When the direction switch 124 is in the upper position as shown in FIG. 7, the optical coupler 92 functions as a "counter" coupler by supplying the clock input signals to the flip-flops, while the coupler 94 functions as a "direction indicator" coupler by controlling the preset inputs. The pulse train on the line 123 is supplied through the switch 114 to the clock inputs of both the flip-flops 134 and 136. When the input shaft 62 is rotated in one direction, and a logic "0" to "1" transition occurs at the clock inputs of the flip-flops 134 and 136, the particular flip-flop which is enabled by having its preset input at logic "1" will generate a "1" to "0" transition signal at its Q output terminal. Depending on which flip-flop has been enabled, the "1" to "0" transition output signal will be supplied to either the UP input or DOWN input of the counter 140 which causes the counter to increment or decrement the count accordingly. The other flip-flop, which at this time is disabled by having its preset input at logic "0", will maintain its Q output at logic "1" and thus not affect the count of the counter.

If the direction switch 124 remains in the upper position and the input shaft 62 is rotated in an opposite direction, the logic "0" to "1" transitions at the clock inputs will occur when the preset inputs have been inverted. Thus, the flip-flop which is disabled by a logic "0" at the preset input when the input shaft is rotated in one direction, will be enabled when the input shaft is rotated in the opposite direction such that the count of the counter 140 is incremented or decremented in accordance with the output of the enabled flip-flop.

If the direction switch 124 is moved to the lower position, the functions of the couplers 92 and 94 are reversed. In this case, the coupler 94 functions as the counter coupler by supplying the clock input signals, while the coupler 92 will function as the direction indicator coupler by controlling the preset inputs.

Figure 9:
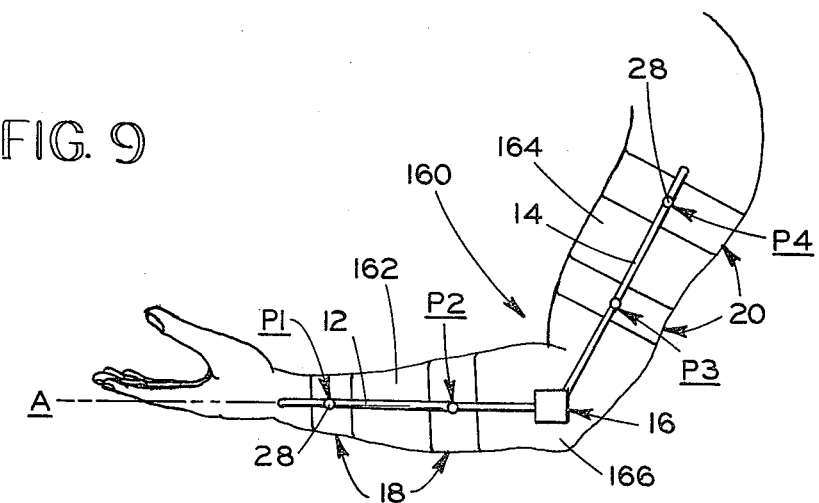
FIGS. 9–11 are diagrammatic views illustrating the operational position of the instrument as utilized in determining the angular displacement between two body portions of an arm.
Figure 10:
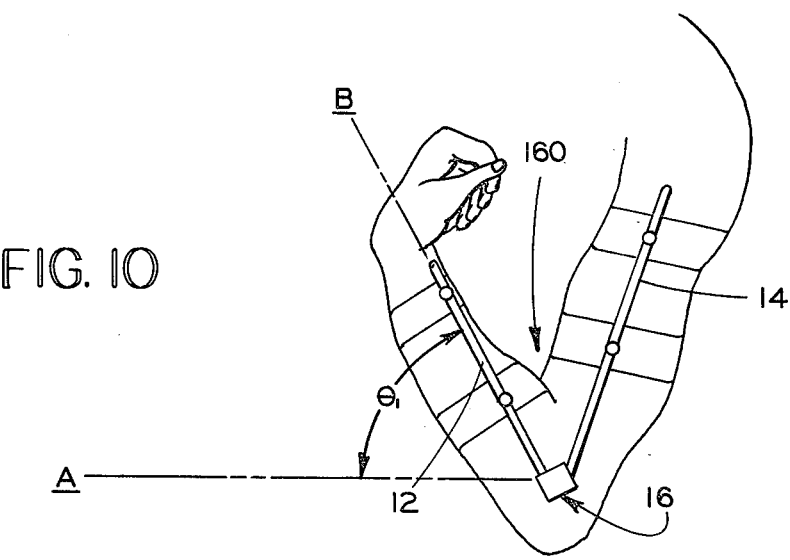
Figure 11:
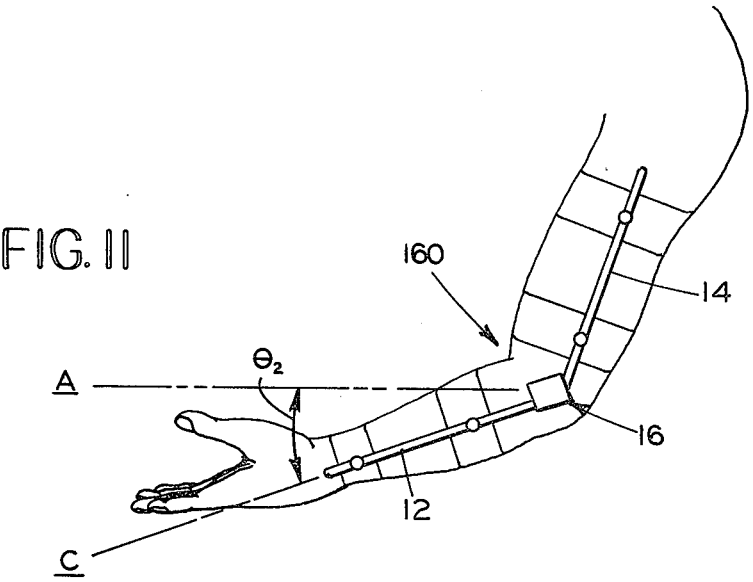

Referring to FIGS. 9 through 11, the measuring instrument 10 according to the present invention is shown in operative position on an arm 160 having a forearm 162 and an upper arm 164 connected to a common elbow joint 166. As shown in FIG. 9, the elongate rod 12 is secured in spaced relation at two predetermined points P1 and P2 along the forearm 162 by the support means 18, while the elongate rod 14 is secured in spaced relation at two predetermined support points P3 and P4 along the upper arm 164 by the support means 20. By utilizing the ball and socket asemblies 28 at the predetermined support points, the forearm 162 and upper arm 164 can be rotated about the elbow joint 166 without the instrument 10 affecting the natural movements of the arm.

The particular points along a body portion at which the ball and socket assemblies 28 are to be positioned will vary from applications to application. For example, when positioning the support means 18 on a forearm, the ball and socket assemblies 28 can be positioned to maintain the elongate rod 12 in generally parallel relationship with either of the two bones, the radius or the ulna (not shown), which extend through the forearm. If the elongate rod 12 is supported in parallel relationship with the radius, for example, the ball and socket assemblies 28 will permit the natural twisting between the radius and the ulna as the forearm is rotated about the elbow joint.

Another important feature of the present invention includes the manner in which the elongate rods are connected to the encoder 16. As previously mentioned, the elongate rods 14 are mounted to permit the plane of rotation of the rods 14 to vary with respect to the plane of rotation of the rod 12. The plane of rotation of the rod 12 is also adjustable. This enables the instrument to be supported on two body portions connected to a common joint having planes of rotation which are offset from one another.

The instrument according to the present invention is especially advantageous for use with individuals who have sustained some type of injury with respect to a body joint and must undergo treatment such as physical therapy in order to regain full use of the two body portions connected to the joint. The instrument can be used to determine the initial range of motion between two body portions. Thereafter, the instrument can be used on a regular basis to provide an indication of any improvement in movement which may result from the therapy sessions.

Referring again to FIG. 9, assume that the position of the arm shown represents the furthest extension which an individual can comfortably obtain. When the arm is in this position, the reset switch 142 in the counter and display circuit 24 is actuated to clear the counter 140 and zero the LED display 150. This position, represented as position A in FIG. 9, defines the "zero anatomical" position. The direction switch 124 is then set such that, when the arm is moved upwardly, the counter 140 counts in the up mode. When the forearm is rotated upwardly to its furthest position, represented as position B in FIG. 10, the LED display 150 will then indicate in degrees the value of the angle $\theta_1$, which represents the relative angular range of motion between the forearm 162 and the upper arm 164.

After the arm has been moved back to the zero anatomical position A, the direction switch 124 can be moved to the opposite position and the individual can attempt to further extend his arm in order to measure any further extension (position C) from the position A. This further extension, represented as angle $\theta_2$ in FIG. 11, would be displayed in degree values by the LED display 150.

Although the above-described embodiment of the instrument is specifically designed for use in measuring the range of motion associated with either a knee or elbow joint, the instrument can readily be modified to measure the range of motion associated with other body joints. Basically, these modifications would include varying the length of the elongate rods in accordance with the length of the associated body portion and, in instances when the straps 20 could not provide a suitable support, providing alternative means for fixing the ball and socket assemblies 28 to the body portion.

It should be noted that the present invention, in its broadest sense, encompasses the idea of supporting each of the elongate rods on the respective body portion in spaced relation to the body portion and maintaining the elongate rod in spaced relation to the body portion without limiting the natural movement of the body portion as the same is rotated about the common joint. In most instances, this spaced relation will also be a parallel relation to the body portion.

In accordance with the provisions of the patent statutes, the principle and mode of operation of the invention have been explained and illustrated in its preferred embodiment. However, it must be understood that the invention can be practiced otherwise than as specifically illustrated and described without departing from its spirit or scope.

What is claimed is:

1. An apparatus intended for use in measuring the relative angular displacement between two body portions connected to a common joint comprising:
    a first elongate member;
    a first support means adapted to be connected to a first one of two body portions connected to a common joint for supporting said first elongate member in generally spaced relation to the first body portion, said first support means maintaining said first elongate member in spaced relation to the first body portion as the first body portion is rotated about the common joint;
    a second elongate member;

a second support member adapted to be connected to a second one of the two body portions for supporting said second elongate member in generally spaced relation to the second body portion, said second support means maintaining said second elongate member in spaced relation to the second body portion as the second body portion is rotated about the common joint;

means for pivotally interconnecting said first and second elongate members including an encoder means for generating an output signal representing the relative angular position between said first and second elongate members; and means coupled to said interconnecting means and responsive to said encoder output signal for determining an angular displacement measurement between said first and second elongate members, said measurement representing the relative angular displacement between the two body portions, said measuring means including a display means for displaying said angular displacement mesurement, means for generating a reset signal defining an initial angular position between said elongate members, said measuring means responsive to said reset signal for determining said angular displacement measurement relative to said initial angular position.

2. An apparatus according to claim 1 wherein said first elongate member has a longitudinal axis and said first support means includes means for positioning said first elongate member with the longitudinal axis of said first member in general parallel relation to the first body portion and maintaining said first elongate member in generally parallel relation to the first body portion as the first body portion is rotated about the common joint.

3. An apparatus according to claim 2 wherein said second elongate member has a longitudinal axis and said second support means includes means for positioning said second elongate member with the longitudinal axis of said second member in generally parallel relation to the second body portion and maintains said second elongate member in generally parallel relation to the second body portion as the second body portion is rotated about the common joint.

4. An apparatus according to claim 1 wherein said first support means includes a pair of individual supports coupled to said first elongate member and means for mounting each of said individual supports on the first body portion in spaced relation to one another.

5. An apparatus according to claim 4 wherein at least one of said individual supports includes a ball and socket assembly, said ball having an aperture formed therethrough for receiving said first elongate member.

6. An apparatus according to claim 4 wherein said mounting means includes a pair of straps each having one of said individual supports secured thereto, said straps including means for fastening the ends thereof when said straps have been wrapped around the first body portion.

7. An apparatus according to claim 4 wherein said second support means includes a pair of individual supports coupled to said second elongate member and means for mounting each of said individual supports on the second body portion in spaced relation to one another.

8. An apparatus according to claim 1 wherein said interconnecting means includes means for mounting at least one of said elongate members for limited relative movement along an axis perpendicular to a plane in which said elongate member is pivoted.

9. An apparatus according to claim 1 wherein said measurement means determines a first angular displacement value when said first and second elongate members are pivoted towards one another from said initial angular position and determines a second angular displacement value when said first and second members are pivoted away from one another from said initial angular position.

10. An apparatus intended for use in measuring the relative angular displacement between two body portions connected to a common joint comprising:

a first elongate member;

a first support means adapted to be connected to a first one of two body portions connected to a common joint for supporting said first elongate member in generally spaced relation to the first body portion, said first support means including a pair of ball and socket assemblies, each of said balls having an aperture formed therethrough for receiving said first elongate member, and means for mounting each of said ball and socket assemblies on the first body portion in spaced relation to one another;

a second elongate member;

a second support means adapted to be connected to a second one of the two body portions for supporting said second elongate member in generally spaced relation to the second body portion;

means for pivotally interconnecting said first and second elongate members; and means coupled to said interconnecting means for measuring the relative angular displacement between said first and second elongate members, said measurement representing the relative angular displacement between the two body portions.

11. An apparatus according to claim 10 wherein said second support means includes a pair of ball and socket assemblies, each of said balls having an aperture formed therethrough for receiving said second elongate member, and means for mounting each of said ball and socket assemblies on the second body portion in spaced relation to one another.

* * * * *